United States Patent [19]

Wagner

[11] Patent Number: 5,507,211

[45] Date of Patent: Apr. 16, 1996

[54] RELEASABLE SOCKET

[75] Inventor: Erik J. Wagner, Allen, Tex.

[73] Assignee: AMEI Technologies Inc., Wilmington, Del.

[21] Appl. No.: 265,005

[22] Filed: Jun. 23, 1994

[51] Int. Cl.⁶ ................................................. B25B 23/55
[52] U.S. Cl. ................................................. 81/472; 81/125
[58] Field of Search ........................ 81/125, 472, 121.1, 81/124.4

[56]        References Cited

U.S. PATENT DOCUMENTS

| | | | |
|---|---|---|---|
| 1,164,073 | 12/1915 | Cunningham | 81/472 |
| 2,798,394 | 7/1957 | Hubbard | 81/125 |
| 4,060,113 | 11/1977 | Matsushima | 81/125 |
| 5,199,331 | 4/1993 | Tsukamoto | 81/125 X |
| 5,304,179 | 4/1994 | Wagner | 606/61 |
| 5,309,798 | 5/1994 | Markwart et al. | 81/438 |

*Primary Examiner*—James G. Smith
*Attorney, Agent, or Firm*—Baker & Botts

[57]        ABSTRACT

A handling tool is provided for installing fastening devices such as pedicle screws in a constrained or limited space. The fastening device may be releasably secured with the handling tool to simplify installation procedures. The handling tool includes a one piece, releasable socket having a cavity sized to receive a portion of the fastening device therein. One or more flexible arms may be formed as an integral part of the socket for releasably securing the fastening device within the cavity. For some applications a plurality of flexible arms and/or longitudinal slots may be formed in the handling tool to limit the amount of torque applied to the fastening device.

2 Claims, 3 Drawing Sheets

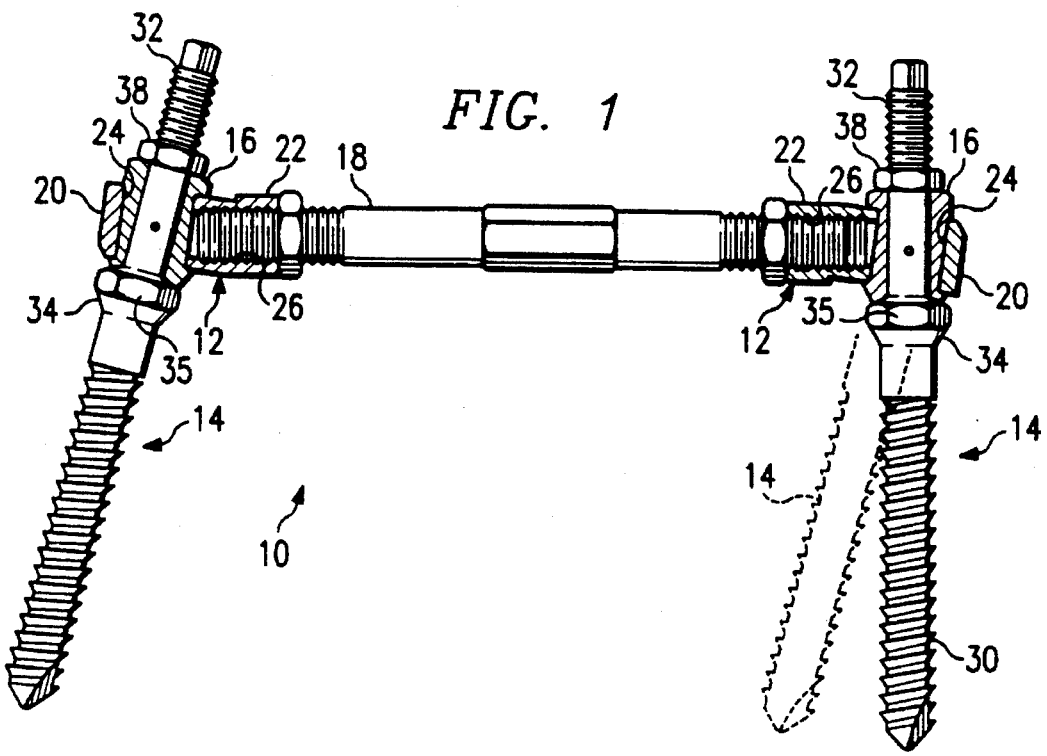
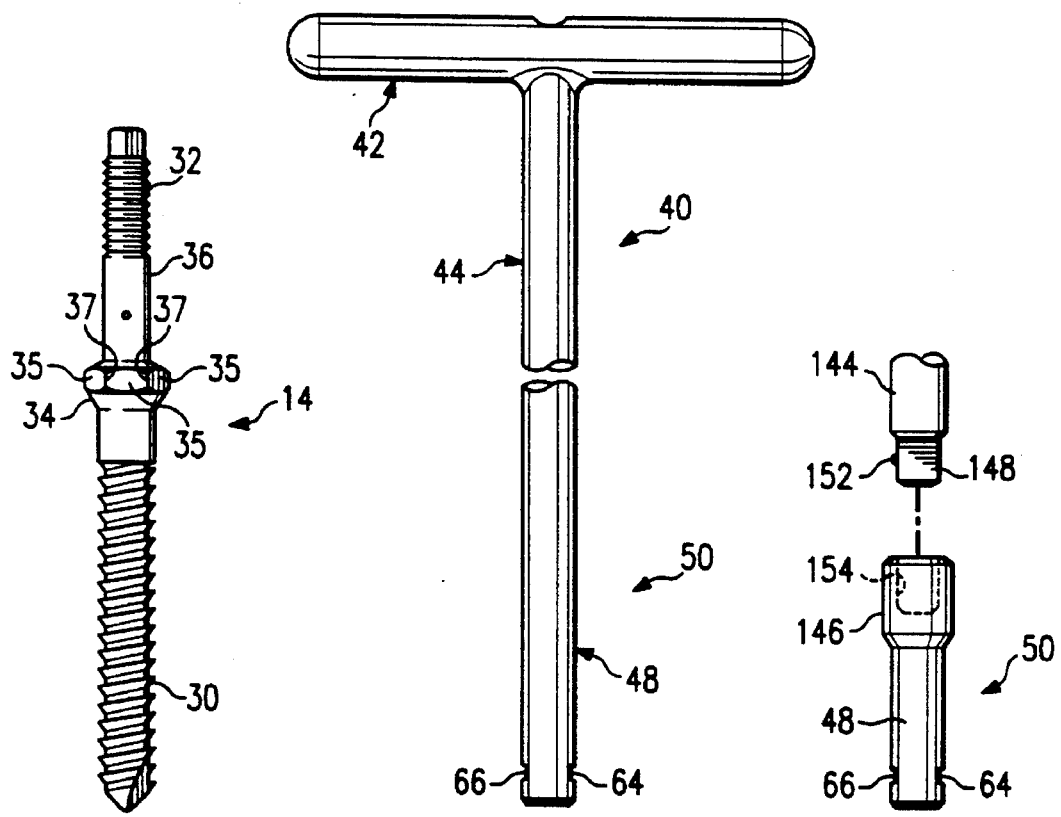
FIG. 1
FIG. 2    FIG. 3A    FIG. 3B

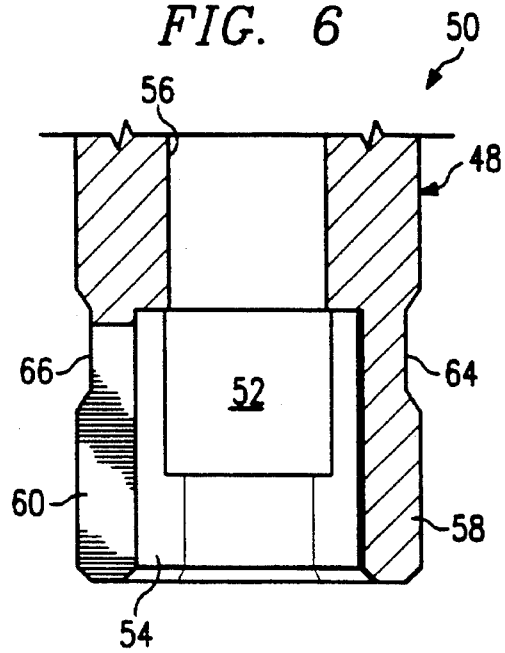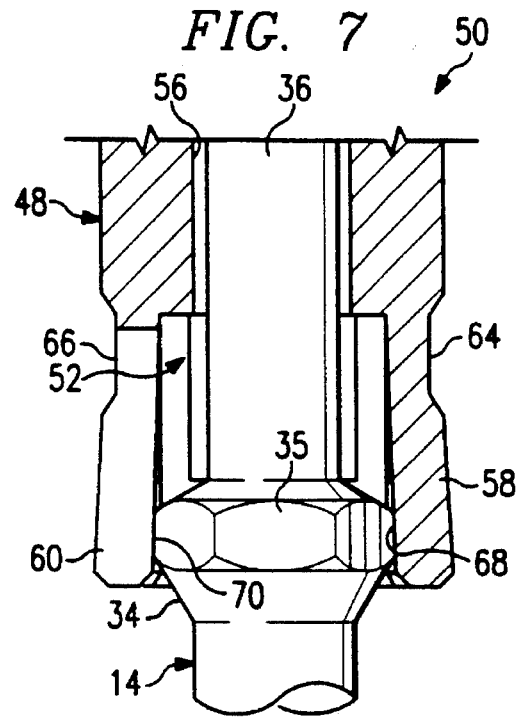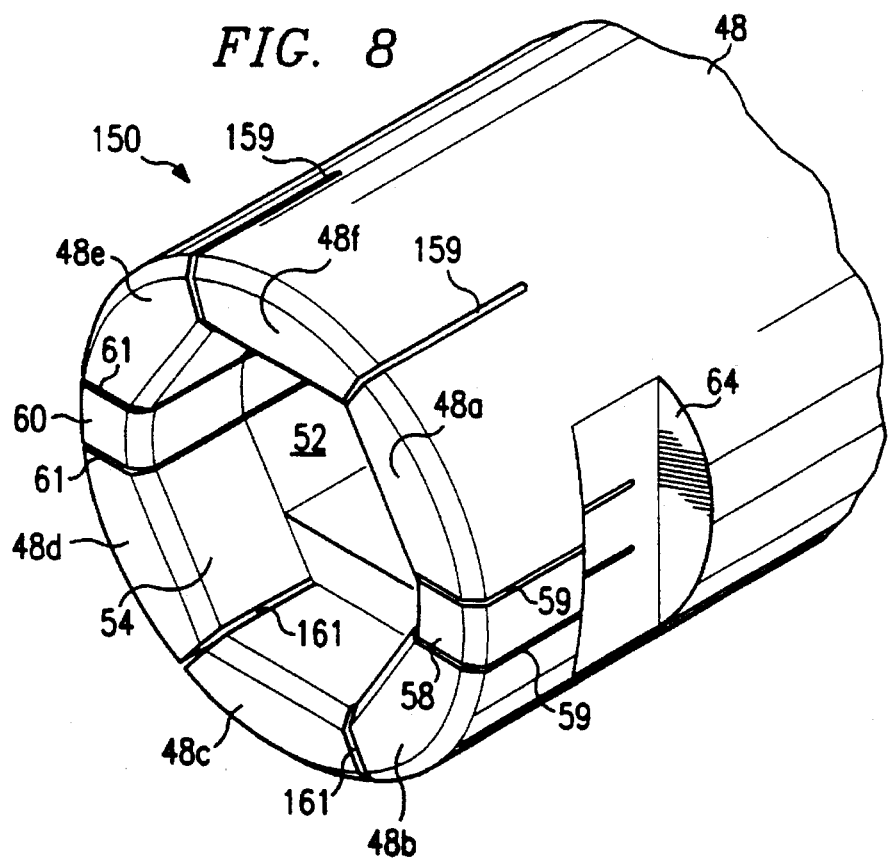

[5,507,211]

RELEASABLE SOCKET

TECHNICAL FIELD OF THE INVENTION

This invention relates in general to the field of hand tools for releasably holding a fastening device and more particularly to a handling tool used during surgical procedures to install a spinal fixation system having pedicle screws.

BACKGROUND OF THE INVENTION

Spinal fixation, such as lumbar sacral fusion and the correction of spinal deformity such as scoliotic curves, is a well known and frequently used medical procedure. Pedicle, lateral and oblique mounting means may be used to secure corrective spinal instrumentation to a portion of the patients' spine that has been selected for fusion by arthrodesis.

A spinal fixation system often comprises corrective spinal instrumentation which may be attached to selected vertebrae of the spine by screws, hooks and clamps. The corrective spinal instrumentation may include spinal rods or plates, which are generally installed parallel to the patients' back. The correct spinal instrumentation may further include connecting rods which extend between the spinal rods or plates. A spinal fixation system may be used to correct problems in the lumbar and thoracic portions of the spine, and may often be installed posture the spine on opposite sides of the spinous process and adjacent to the transverse process. Examples of pedicle screws and other types of fastening devices used with spinal fixation systems are shown in U.S. Pat. Nos. 4,763,644; 4,805,602; 4,887,596; 4,950,269; 5,129,388 and 5,304,179. These patents are incorporated by reference for all purposes within this Application.

When a threaded fastening device or component such as a screw, nut or bolt must be fitted into a constrained space, it is often preferable to have the fastening device or component releasably engaged with the tightening tool or handling tool. Secure, but at the same time releasable, engagement between the tightening tool and fastening device is particularly important during surgical and other medical procedures. By releasably engaging the fastening device with its associated handling tool, procedures for installing the fastening device may be simplified and the need to hold the component with one hand while using the other hand to initiate rotation or threading may be eliminated. Again, during many medical procedures such as spinal fixation, very little space is available for using more than one tightening or handling tool. Also, dropping or accidently releasing a fastening device during surgery may have serious adverse consequences.

SUMMARY OF THE INVENTION

In accordance with the present invention, a socket is provided which substantially eliminates or reduces the disadvantages and problems associated with prior handling tools and tightening tools associated with installing fastening devices in a constrained or limited space. One embodiment of the present invention provides a one piece, releasable socket which may be used to pick up and install a variety of fastening devices such as bolts, nuts and screws. The socket preferably includes a body having a cavity extending at least partially therethrough. An opening to the cavity preferably includes an irregularly shaped geometry with at least one interference point having a smaller dimension than the component or fastening device which will be installed by the socket.

In one aspect of the present invention a handling tool is provided having a body with a cavity formed therein and an opening for placing a fastening device or component within the cavity. One or more interference points are preferably provided within the cavity to releasably secure the fastening device or component therein. Each interference point is preferably formed on a flexible finger which may be deflected radially outward by inserting the fastening device into the cavity to releasably secure the fastening device with the handling tool.

Technical advantages of the present invention include providing a one piece, releasable socket which does not require the use of springs, clips, balls or plungers to releasably hold a fastening device within the socket. By providing a one piece, releasable socket problems associated with cleaning and sterilizing the socket prior to conducting a surgical procedure are substantially reduced or eliminated. Also, the cost associated with manufacturing a one piece, releasable socket may be substantially reduced as compared to other types of releasable sockets or handling and tightening tools. For many applications, the present invention allows reducing the overall dimension of the socket or handling tool as compared to other types of tools having balls, springs, clips, or plungers for releasing a fastening device. Again, manufacturing costs and maintenance costs may be substantially reduced by providing a one piece, releasable socket in accordance with the teachings of the present invention.

Other technical advantages of the present invention include providing a handling tool with one or more flexible arms to releasably secure a fastening device with the handling tool. For some applications, the handling tool may include multiple flexible arms and/or longitudinal slots which limit the amount of torque which can be applied to the fastening device by the handling tool.

BRIEF DESCRIPTION OF THE DRAWINGS

For a more complete understanding of the present invention, and for further features and advantages, reference is now made to the following descriptions, taken in conjunction with the accompanying drawings, in which:

FIG. 1 is a side view partially in section and partial in elevation of a spinal fixation system having a pair of pedicle screws which may be installed by a handling tool incorporating the present invention;

FIG. 2 is a drawing in elevation showing an example of a fastening device (pedicle screw) which may be installed by a handling tool incorporating the present invention;

FIG. 3A is a schematic drawing in elevation with portions broken away showing a handling tool or tightening tool and a one piece, releasable socket formed as an integral part thereof incorporating one embodiment of the present invention;

FIG. 3B is a schematic drawing in elevation with portions broken away showing a handling tool or tightening tool with a separate one piece, releasable socket incorporating another embodiment of the present invention;

FIG. 6 is a drawing partially in section and partially in elevation with portions broken away taken along line 6—6 of FIG. 5;

FIG. 7 is a drawing partially in section and partially in elevation with portions broken away showing the pedicle screw of FIG. 2 releasably secured within the socket of FIG. 6; and FIG. 8 is an enlarged isometric drawing with portions broken away showing the socket of FIG. 4 modified in accordance with a further embodiment of the present invention to limit the torque applied to a fastening device releasably secured therein.

DETAILED DESCRIPTION OF THE INVENTION

Figure 4:
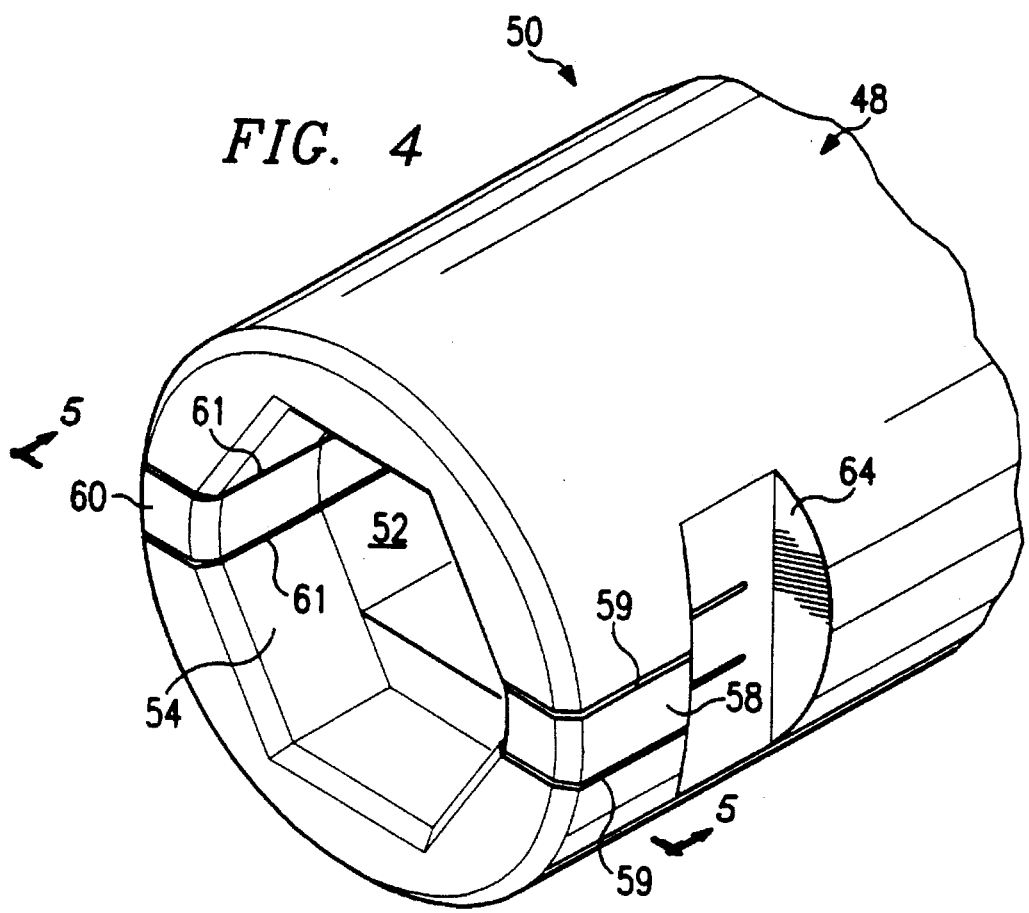
FIG. 4 is an enlarged isometric drawing with portions broken away showing the socket of FIGS. 3A and 3B.

The preferred embodiments of the present invention and its advantages are best understood by referring to FIGS. 1 through 8 of the drawings, like numerals being used for like and corresponding parts of the various drawings.

FIG. 1 shows spinal fixation system 10 which comprises connectors 12, pedicle screws 14, cam bushings 16 and spinal instrumentation 18. Connectors 12 further comprise a first portion 20 and a second portion 22. First portion 20 of connector 12 includes a first opening 24 extending therethrough. Second portion 22 of connector 12 has a second opening 26 which extends at least partially therethrough and is arranged longitudinally relative to second portion 22 of connector 12. First portion 20 of connector 12 may be positioned at an angle of approximately 7.5° relative to second portion 22. Spinal instrumentation 18 may comprise a spinal rod, spinal plate, cable, or any other mechanism associated with spinal fixation system 10.

Pedicle screws 14 may be installed in selected vertebrae (not shown) of a patient's spine (not shown). Annular shoulder or enlarged portion 34 is preferably formed on the exterior of each pedicle screw 14 intermediate the ends thereof. The remainder of spinal fixation system 10 may be placed on pedicle screws 14 to accommodate the desired angle for insertion of each pedicle screw 14 into the selected vertebrae (not shown). Spinal fixation system 10 may be fastened to pedicle screws 14 so that spinal instrumentation 18 is substantially parallel with the patients' spine.

Cam bushings 16 may be placed in respective connectors 12 which are typically coupled to opposite ends of spinal instrumentation 18. When desired to attach connectors 12 to positive pedicle screws angles, connectors 12 are angled away from the vertebrae. Negative pedicle screw angles are accommodated by angling connector 12 towards the vertebrae. Details concerning the design function and installation of spinal instrumentation system 10 are contained in U.S. Pat. No. 5,304,179 entitled, "System and Method for Installing a Spinal Fixation System at Variable Angles".

As best shown in FIG. 2, pedicle screw 14 further includes a first threaded portion 30 for attachment to selected portions of a patient's vertebrae, annular shoulder 34 and second threaded portion 32. Pedicle screw 14 also includes a relatively smooth outside diameter portion 36 disposed between annular shoulder 34 and second threaded portion 32. These features of pedicle screw 14 are designed for compatibility with spinal fixation system 10. Handling tool or tightening tool 40, representing only one embodiment of the present invention, is shown in FIG. 3A for use during installation of pedicle screws 14. However, the present invention may be used with a wide variety of fastening devices including nuts, bolts and screws. For example, handling tool 40 could be used to tighten nut 38 with second threaded portion 32 of the respective pedicle screw 14.

Handling tool 40, which may also be described as a tightening tool, has a generally T-shaped configuration defined in part by handle 42 and shaft 44. End 48 of shaft 44 opposite from handle 42 may be generally described as a cylindrical body which preferably includes one piece, releasable socket 50 formed as an integral part thereof. As will be readily apparent to those skilled in the art, socket 50 may be incorporated into various types of hand tools, power tools and other devices used for installation of threaded fasteners in addition to handling tool 40. Also, socket 50 may be part of a separate, individual tool as shown in FIG. 3B. For some applications, a plurality of sockets with different dimensions and configurations may be included as part of a set for installing a wide variety of fastening devices.

As shown in FIG. 3B, socket 50 may be formed as a separate tool with coupling means 146 provided as a portion thereof. A compatible coupling means 148 may be provided on shaft 144 to allow releasably attaching socket 50 to a wide variety of handling and tightening tools. For the embodiment shown in FIG. 3B, coupling means 148 comprises square shoulders along with ball detent 152 which are sized to be received within recess 154 of coupling means 146. FIGS. 3A and 3B show representation examples of only two ways in which socket 50 may be used with a handling tool or tightening tool.

As shown in FIGS. 1 and 2, annular shoulder 34 of pedicle screw 14 includes a plurality of flat surfaces 35 which partially define a generally hexagon shaped perimeter. A plurality of corners or vertical edges 37 are preferably formed by adjacent flat surfaces 35 to further define the hexagon shaped perimeter on annular shoulder 34.

As best shown in FIGS. 4 through 7, cavity 52 disposed in cylindrical body 48 of socket 50 preferably includes opening 54 having an irregularly shaped hexagon configuration corresponding approximately with flat surfaces 35 and corners 37 on the exterior of annular shoulder 34. Longitudinal bore 56 may also be formed within socket 50 to communicate with cavity 52 and receive second threaded portion 32 and smooth outside diameter portion 36 of pedicle screw 14 therein.

Socket 50 may include a pair of flexible arms 58 and 60 formed in the exterior of cylindrical body 48 on opposite sides of opening 54. Flexible arm 58 may be formed by cutting a pair of parallel slots 59 longitudinally through an exterior portion of cylindrical body 48. In the same manner flexible arm 60 may be formed by cutting a pair of parallel slots 61 longitudinally through an exterior portion of end 48 opposite from flexible arm 58. Various machining procedures may be used to form parallel slots 59 and 61 including laser cutting, electron discharge machining (EDM), and saw cutting. Cutouts 64 and 66 may be formed partially through the exterior of cylindrical body 48 to increase the flexibility of the respective arms 58 and 60. For some applications EDM may be used to form cavity 52 including opening 54 and bore 56 along with cutouts 64 and 66.

As previously noted opening 54 preferably has a configuration corresponding approximately with flat surfaces 35 and corners 37 on the exterior of annular shoulder 34. The dimensions of opening 54, except for arms 58 and 60, are generally slightly larger than the corresponding dimensions associated with annular shoulder 34 to allow pedicle screw 14 to be easily inserted into and removed from cavity 52.

Figure 5:
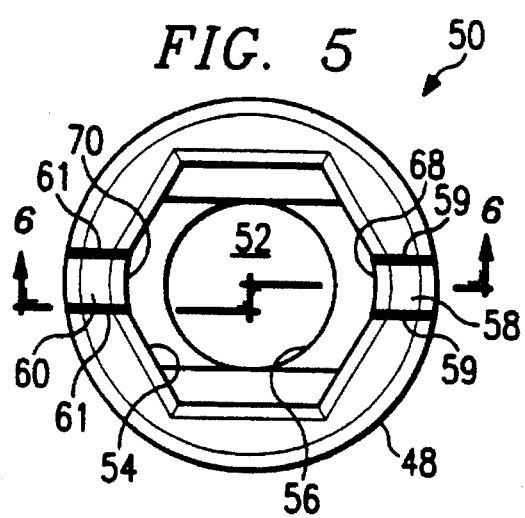
FIG. 5 is a drawing showing an end view of the socket FIG. 4.

As best shown in FIG. 5, flexible arms 58 and 60 preferably include respective radii 68 and 70 disposed within opening 54 on opposite sides of cavity 52. Radii 68 and 70 result in opening 54 having an irregularly shaped hexagon configuration as compared to annular shoulder 34 on pedicle screw 14. The dimensions associated with each radius 68 and 70 are selected such that an interference contact is created with the corresponding corner 37 of the hexagon perimeter of annular shoulder 34 during insertion of pedicle screw 14 into socket 50. As best shown in FIG. 7, the interference fit between annular shoulder 34 and radii 68 and 70 results in radial or outward deflection of the respective flexible arms 58 and 60. This deflection results in releasably trapping pedicle screw 14 within socket 50.

Pedicle screw 14 may be inserted into cavity 52 until annular shoulder 34 is disposed within opening 54. Opposite corners 37 associated with flat surfaces 35 will cause flexible arms 58 and 60 to deflect radially outward to releasably secure pedicle screw 14 with socket 50. Handle 42 may then be used to rotate handling tool 40 along with pedicle screw 14 disposed within socket 50. As torque is applied to pedicle screw 14 by socket 50 opening 54 will contact flat surfaces 35 and corners 37 and create "hoop stress" within opening 54. As will be explained later in more detail, by providing additional longitudinal slots 159 and 161 and/or additional flexible arms 58 and 60, this hoop stress may be used to limit the amount of torque applied to pedicle screw 14.

The amount of force necessary to deflect the flexible arms 58 and 60 may be selected as desired for the particular type of fastening device which will be installed with the associated socket 50. The force may be varied by adjusting the depth of cutouts 64 and 66, varying the spacing between the respective pairs of longitudinal slots 59 and 61 varying the length of longitudinal slots 59 and 61 and adjusting the amount of interference contact between annular shoulder 34 and flexible arms 58 and 60 or by changing or modifying the material. Thus, a one piece, releasable socket may be modified in accordance with the teachings of the present invention to accommodate a wide variety of fastening devices having various geometric configurations and weights.

The configuration of opening 54 and cavity 52 may also be modified as required to accommodate the exterior configuration of various fastening device which will be releasably secured in the associated socket. For example, opening 54 may have a rectangular, square, circular or oval configuration. For some applications, socket 50 may only require one flexible arm with an associated interference contact to releasably secure a fastening device therein. For other applications, additional flexible arms with a corresponding interference contact may be provided as part of socket 50. Finally, the interference contact between a flexible arm and the associated fastening device may be provided by a concave surface such as radii 68 and 70 shown in FIG. 5 or by appropriately sized convex surfaces (not shown) or any other suitable projection to establish the desired interference fit with the selected fastening device.

For some applications additional longitudinal slots 159 and 161 may be formed in the exterior of cylindrical body 48 and/or additional flexible arms 59 and 60 provided. The amount of rotational torque which socket 50 can apply to annular shoulder 34 or any other fastening device disposed therein will be limited by providing these additional longitudinal slots and/or flexible arms. Such torque limits may be very beneficial for some medical procedures and other applications.

Socket 150 shown in FIG. 8 is essentially the same as previously described socket 50 except for the additions of multiple slots 159 and 161. Slots 59, 61, 159 and 161 cooperate with each other to divide the end of socket 150 into segments designated 48a, 48b, 48c, 48d, 48e and 48f. These segments along with flexible arms 58 and 60 limit the amount of torque which socket 150 can apply to annular shoulder 34 or a similar fastening device disposed within opening 54. When the torque limit is exceeded, segments 48a, 48b, 48c, 48d, 48e, and 48f can flex radially outward with respect to each other and flexible arms 58 and 60 such that socket 150 can rotate with respect to flat surfaces 35 and corners 37 on annular shoulder 34. By varying the number of slots 159 and 161 and/or flexible arms 58 and 60 formed within socket 150 or material, limits for the amount of torque that can be applied to pedicle screw 14 may be selected as desired for specific applications. Thus, one embodiment of the present invention provides a one-piece socket which may be releasably secured with a fastening device and which may also function as a torque limiting device. The use of multiple slots 159 and 161 and/or multiple flexible arms 58 and 60 substantially reduces the cost of the respective handling tool as compared to previous torque limiting devices associated with surgical equipment.

Although the present invention has been described with several embodiments, various changes and modifications may be suggested to one skilled in the art, and it is intended that the present invention encompasses such changes and modifications as fall within the scope of the following claims.

What is claimed is:

1. A one piece socket having a body for releasably securing a fastening device therein comprising:

a cavity formed within the body and extending at least partially therethrough, the cavity having an opening sized to receive a selected portion of the fastening device therein;

at least one flexible arm formed in the exterior of the body as an integral part thereof adjacent to the cavity;

a portion of each flexible arm projecting into the cavity to form an interference fit with an adjacent portion of the fastening device whereby the fastening device may be releasably secured within the body by inserting the portion of the fastening device into the opening to form the interference fit; and a plurality of slots formed in the exterior of the body and extending longitudinally from the opening whereby the slots cooperate with each other to limit the amount of torque which may be applied by the socket to the portion of the fastening device releasably secured within the body.

2. A socket having a body for releasably securing a fastening device therein comprising:

a cavity formed within the body and extending at least partially therethrough, the cavity having an opening sized to receive a selected portion of the fastening device therein;

at least one flexible arm formed in the exterior of the body adjacent to the cavity;

a portion of each flexible arm projecting into the cavity to form an interference fit with an adjacent portion of the fastening device whereby the fastening device may be releasably secured within the body by inserting the portion of the fastening device into the opening to form the interference fit;

each flexible and formed by a pair of longitudinal slots extending from the opening through the exterior of the body adjacent to the cavity; and a cutout formed in the exterior of the body adjacent to the end of each flexible arm opposite from the opening to adjust the amount of force required to deflect the flexible and radially outward with respect to the cavity.

* * * * *